(12) United States Patent
Ketharanathan

(10) Patent No.: US 6,537,313 B2
(45) Date of Patent: *Mar. 25, 2003

(54) SURGICAL PROSTHESES

(76) Inventor: Vettivetpillai Ketharanathan, 132 Barkers Road, Hawthorn, Victoria, 3122 (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/834,544

(22) Filed: Apr. 13, 2001

(65) Prior Publication Data

US 2001/0018618 A1 Aug. 30, 2001

Related U.S. Application Data

(63) Continuation of application No. 08/913,593, filed as application No. PCT/AU96/00126 on Mar. 8, 1996, now Pat. No. 6,262,332.

(30) Foreign Application Priority Data

Mar. 15, 1995 (AU) ................................................ PN1744

(51) Int. Cl.⁷ .............................. A61F 2/06; A61F 2/10; A61F 2/08
(52) U.S. Cl. ................. 623/1.47; 623/15.12; 623/13.11
(58) Field of Search ................................. 623/1.1, 1.13, 623/1.23, 1.32, 1.33, 1.36, 1.41, 1.44, 1.45, 1.46, 1.47, 1.48, 1.5–1.54

(56) References Cited

U.S. PATENT DOCUMENTS

| | | | |
|---|---|---|---|
| 4,047,252 A | | 9/1977 | Liebig et al. |
| 4,319,363 A | | 3/1982 | Ketharanathan |
| 4,553,974 A | | 11/1985 | Dewanjee |
| 4,804,381 A | * | 2/1989 | Turina et al. ............... 435/347 |
| 4,892,539 A | | 1/1990 | Koch |
| 4,986,831 A | | 1/1991 | King et al. |
| 5,002,583 A | | 3/1991 | Pitaru et al. |
| 5,061,276 A | | 10/1991 | Tu et al. |
| 5,282,846 A | | 2/1994 | Schmitt |
| 5,591,225 A | * | 1/1997 | Okuda ....................... 623/1.39 |
| 5,948,654 A | * | 9/1999 | Tranquillo et al. .......... 424/422 |
| 6,136,024 A | * | 10/2000 | Shimizu ..................... 623/1.47 |
| 6,262,332 B1 | * | 7/2001 | Ketharanathan ......... 623/23.72 |

FOREIGN PATENT DOCUMENTS

| | | |
|---|---|---|
| AU | A 58305/86 | 12/1986 |
| AU | A 60596/86 | 1/1987 |
| AU | B 53379/90 | 9/1990 |
| EP | 0522569 A1 | 1/1993 |
| EP | 0637452 A1 | 2/1995 |
| WO | PCT/US90/07233 | 6/1991 |

* cited by examiner

*Primary Examiner*—David H. Willse
*Assistant Examiner*—Hieu Phan
(74) *Attorney, Agent, or Firm*—Stevens & Showalter, LLP

(57) ABSTRACT

A biomaterial is provided which is suitable for use in surgery in a human patient. It includes a coherent layer of non-human collagenous tissue which has been subjected to glutaraldehyde tanning so as to include cross-linked collagen fibrils, and a reinforcement of synthetic material embedded within the coherent layer. The synthetic material has structure features for promoting the embedding, the synthetic material having on average in situ more than 50 of the features per square centimeter.

11 Claims, 18 Drawing Sheets

SURGICAL PROSTHESES

CROSS-REFERENCE TO RELATED APPLICATION

This application is a continuation of U.S. patent application Ser. No. 08/913,593 filed Sep. 12, 1997 now U.S. Pat. No. 6,262,332, which is a 371 of PCT/AU96/00126, filed Mar. 8, 1996.

BACKGROUND OF THE INVENTION

1. Field of the Invention

This invention relates to the field of surgery and more particularly to prosthetic grafts for vascular and non-vascular applications.

2. Description of the Related Art

U.S. Pat. No. 4,319,363 discloses a prosthesis for revascularisation made from a biomaterial and it describes a method for making the prosthesis in which a mesh covered silicon rod (mandril) is inserted into a living host animal, preferably a sheep, collagenous tissue is allowed to grow around the mandril for about twelve to fourteen weeks after which the implant is removed and subjected to glutaraldehyde tanning to form a prosthesis for revascularisation.

BRIEF SUMMARY OF THE INVENTION

The current invention is based on the surprising discovery that certain variations in the structure, geometry and quantity of the synthetic material or substrate on which it is supported promote improved tissue growth and/or allow the creation of new biological composite materials ("biomaterials") suitable for both vascular and non-vascular surgical application.

In accordance with a first broad aspect of the invention there is provided a biomaterial suitable for use in surgery in a human patient, comprising:

a coherent layer of non-human collagenous tissue which has been subjected to glutaraldehyde tanning so as to comprise cross-linked collagen fibrils, and a reinforcement of synthetic material embedded within the coherent layer, said synthetic material having structure features for promoting said embedding, said synthetic material having an average in situ more than 50 of said features per square centimeter.

Preferably, the synthetic material has more than 100 of said features per square centimeter.

Preferably also, the synthetic material is a fibre mesh and the features for promoting said embedding are the reticulations of the mesh. The fibre mesh may be constructed from polyester yarn. The polyester yarn may also be augmented with polyurethane, either in the form of strands of polyester dipped in polyurethane or strands of polyurethane wound around strands of polyester.

Alternatively, the synthetic material may be particulate in nature, in which case said features may be constituted by individual particles of that material.

Preferably further, the biomaterial is in the shape of a tube. Alternatively, the biomaterial is in the form of a sheet.

Preferably also, the biomaterial is smooth on one side to inhibit attachment to surfaces in the patient proximate said one side and rough on the other side to encourage said attachment.

In the case where the synthetic material is a mesh, the mesh may be embedded in the coherent layer such that the mesh structure is in a loose unstretched state.

In accordance with a second broad aspect of the invention there is provided a method of producing a biomaterial, comprising the steps of:

positioning a tubular synthetic fibre mesh structure about a support rod or tube;

implanting the mesh covered support rod or tube in the body of a living, non-human, host animal at such location as to cause growth of collagenous tissue thereon;

allowing said collagenous tissue to grow on the implant until there is formed a coherent wall of said tissue encompassing the rod or tube and having the mesh structure embedded therein;

removing the implant and said coherent wall of collagenous tissue from the body of the host animal;

subjecting said coherent wall of collagenous tissue to glutaraldehyde tanning in order to produce cross-linking of collagen fibrils therein so as to increase the strength of the wall and also to impart immunological inertness and sterility thereto; and removing the rod or tube from within the coherent wall of collagenous tissue at any time subsequent to removal of the rod or tube and coherent wall of collagenous tissue from the body of the host animal;

wherein the tubular synthetic fibre mesh structure fits over the support rod in a loose unstretched state.

Optionally, the tubular mesh may be substantially larger in a longitudinal direction than the support rod or tube.

The tubular biomaterial thereby produced may if desired be cut length-wise to produce a sheet.

In accordance with a third broad aspect of the invention there is provided a method of producing a biomaterial, comprising the steps of:

implanting a support sheet in the body of a living, non-human, host animal at such a location as to cause growth of collagenous tissue thereon;

allowing said collagenous tissue to grow on the implant until there is formed a coherent layer of said tissue on both sides of the support sheet;

removing the implant and said coherent layer of collagenous tissue from the body of the host animal;

subjecting said coherent layer of collagenous tissue to glutaraldehyde tanning in order to produce cross-linking of collagen fibrils therein so as to increase the strength of the layer and also to impart immunological inertness and sterility thereto; and separating the support sheet from the coherent layer of collagenous tissue at any time subsequent to removal of the implant from the body of the host animal to form a pocket, pouch or envelope of collagenous material.

Preferably, a synthetic material having structure features for promoting embedding of the synthetic material within the collagenous tissue is positioned on the support sheet so as to encompass both sides of the support sheet.

Preferably also, the synthetic material is a mesh structure. The synthetic material may have the features required for the first broad aspect of the current invention. The positioning of the synthetic material may be in accordance with the second broad aspect of the invention.

Preferably, for all first, second and third aspects of the invention, the host animal is a sheep. Preferably too, the implant is made beneath the cutaneous muscle of the lateral thoracic wall of the host animal. Preferably further, the implant is allowed in the host animal for at least ten weeks. Preferably also, the tanning step is carried out by immersing the implant and wall of tissue in a bath of buffered glutaraldehyde after removal from the body of the host animal and before removal of the support or tube. Preferably further, the biomaterial is rehydrated for use using heparin.

BRIEF DESCRIPTION OF THE DRAWINGS

In order that the invention may be more clearly understood preferred embodiments of the current invention will be described with reference to the accompanying tables and figures, where:

FIG. 14b shows the primary and secondary cumulative patency of 66 variation II prostheses evaluated by the same surgical unit as shown in FIG. 14a.

DETAILED DESCRIPTION OF PREFERRED EMBODIMENTS OF THE INVENTION

The best method of implementing the improvements the subject of the current invention is to implant the prosthesis in sheep of the following characteristics:

1. Wethers of Border Leicester First Cross, Corriedale, Merino or Polywarth type or any cross breeds of these breeds.
2. Age not less than 3 years and not more than 6 years.
3. Crown to rump length not less than 1 meter.
4. At implant weight not less than 45 kgs.
5. At explant a weight gain of 3 to 5 kgs.

Figure 1:
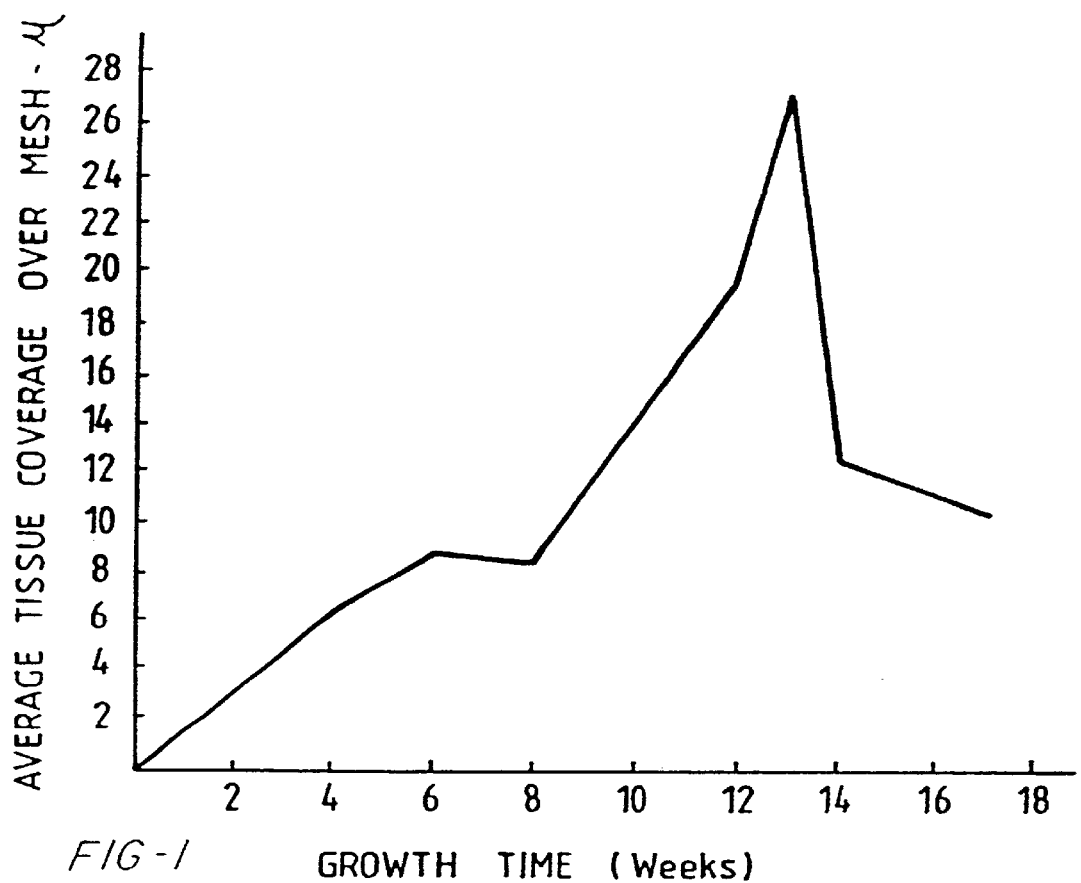
FIG. 1 shows typical tissue growth over the implanted rod or tube over time for one embodiment of the invention.

The biomaterial is explanted between 12 and 14 weeks. With reference to FIG. 1, it can be seen that the maximum tissue coverage occurs at this time.

In the above conditions, sheep provide sterile, self-regulating culture conditions suitable for the reliable and reproducible production of the biomaterial.

Figure 2A:
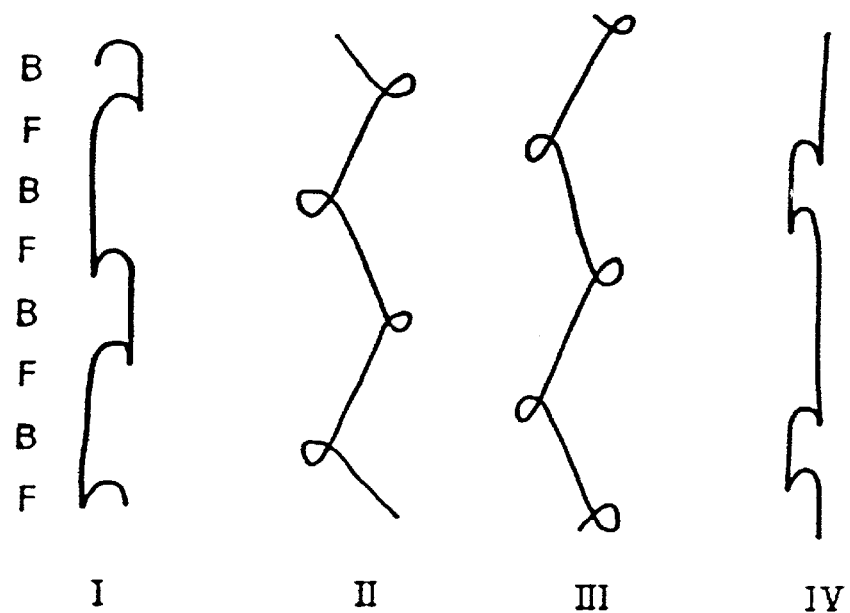
FIG. 2a shows a knotting configuration for Variations I, II, III, IV.
Figure 2:
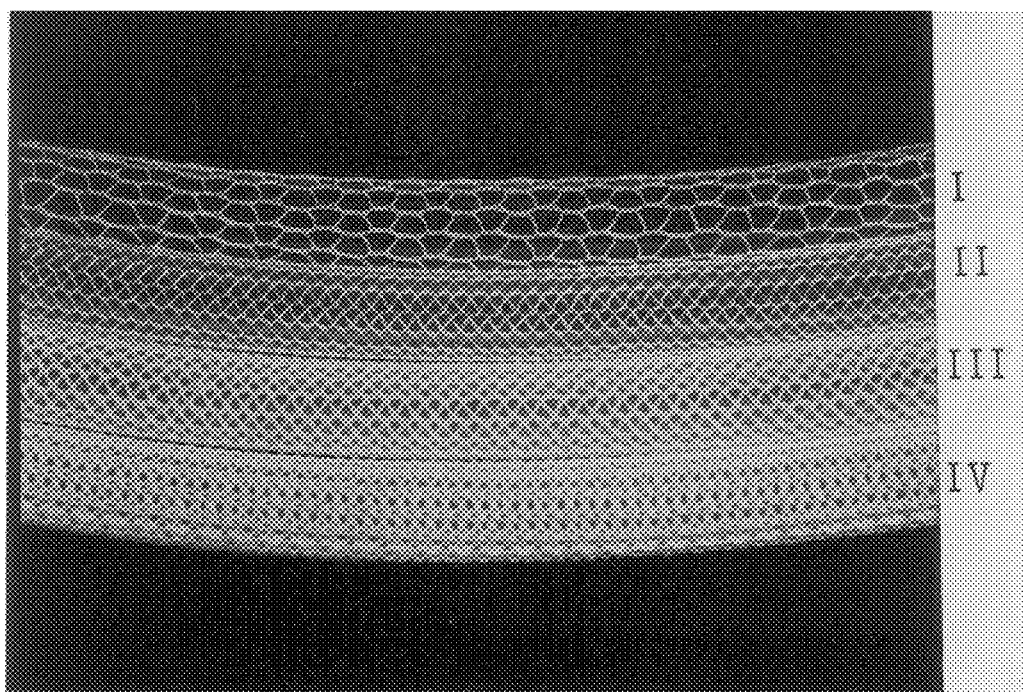
FIG. 2 illustrates four variations in the structure of polyester mesh used in variations II, III and IV of the invention described hereunder. Variation I shown in FIG. 2 is the mesh structure used in U.S. Pat. No. 4,319,363.

Variation I shown in FIG. 2 is the prior art polyester mesh of U.S. Pat. No. 4,319,363.

The different meshes of variations I, II, III and IV were knitted on a Raschel Warp knitting machine with a 2-needle bed and 4-bar structure. The knitted loop structure for each variation was designated as shown in FIG. 2a. The yarn in each case comprised bundles of approximately 50 polyester strands, each strand being composed of two 44 decitex filaments. The resultant yarn density was 0.6 to 0.8 g/m.

Figure 3:
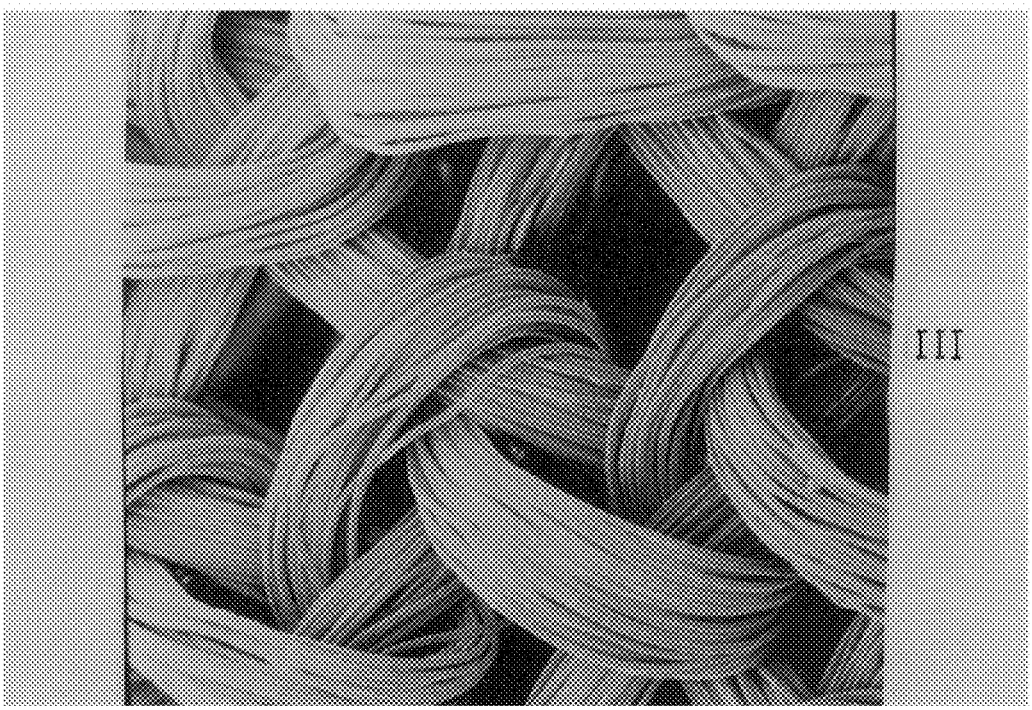
FIG. 3 is a scanning electron microscope (×52) magnification of the fibre structure in variation III of FIG. 2.

In variations V and VI (not demonstrated) woven polyester mesh was dipped in polyurethane in V and polyurethane strands were wound around polyester strands in VI. The mesh knitted structure of variation III is illustrated in FIG. 3.

Modifications in the mandril-mesh assembly influences the eventual tissue incorporation and form. For instance in U.S. Pat. No. 4,319,363, mandril diameter and tubular mesh diameter were identical and the polyester mesh was stretched over the mandril. Illustrating the second aspect of the invention, in variation III an 8 mm diameter tubular mesh was used on a 6 mm diameter mandril. Tubular mesh 106 cm in length was used on a mandril 75 cm in length. This resulted in a thicker and more even cover of tissue over the flow surface without exposed mesh bundles which probably caused less than optimal results in variation I.

In FIGS. 4, 5, 6, 7, 8 and 9, reproduction photomicrographs of the histology sections of mesh variations I, II, III, IV, V and VI demonstrate the changes in tissue configuration and thickness which occurs with the mesh and mesh/mandril modifications. The tissue cover on the flow surface covering the mesh has increased with each variation and the collagenous tissue has become more compact.

Figure 4:
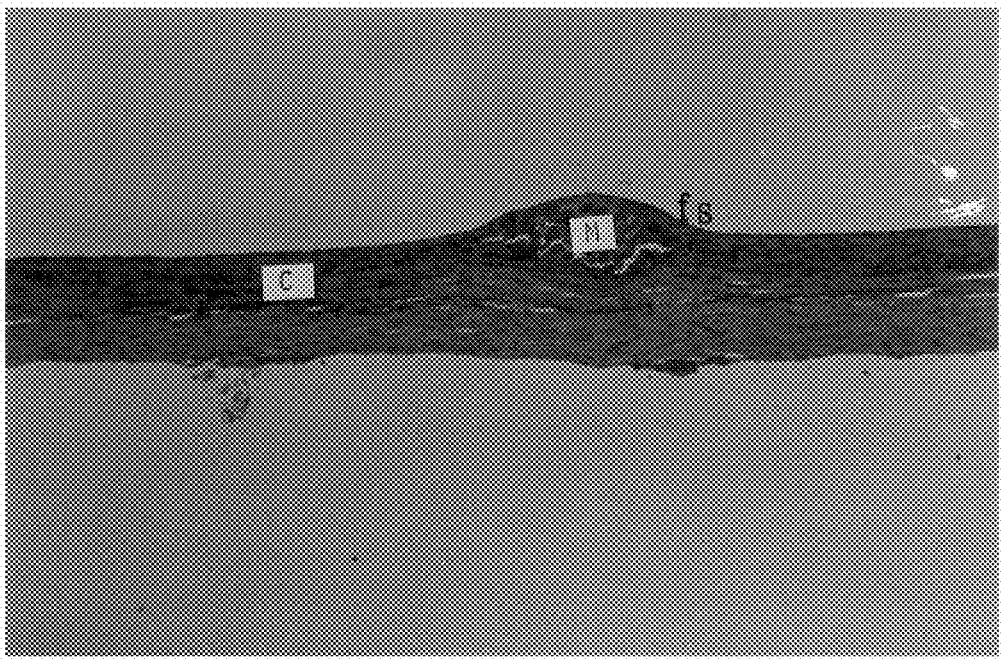
FIG. 4 is a reproduction photomicrograph (H & E×40) showing a section through the pre-flow of variation I, as used in U.S. Pat. No. 4,319,363.

The prior art variation I shown in FIG. 4 shows that polyester mesh strands are in bundles (M) supporting a delicate collagen tissue membrane (C). There is a smooth lining to the flow surface (FS) with a thin tissue cover over the mesh bundles.

Figure 5:
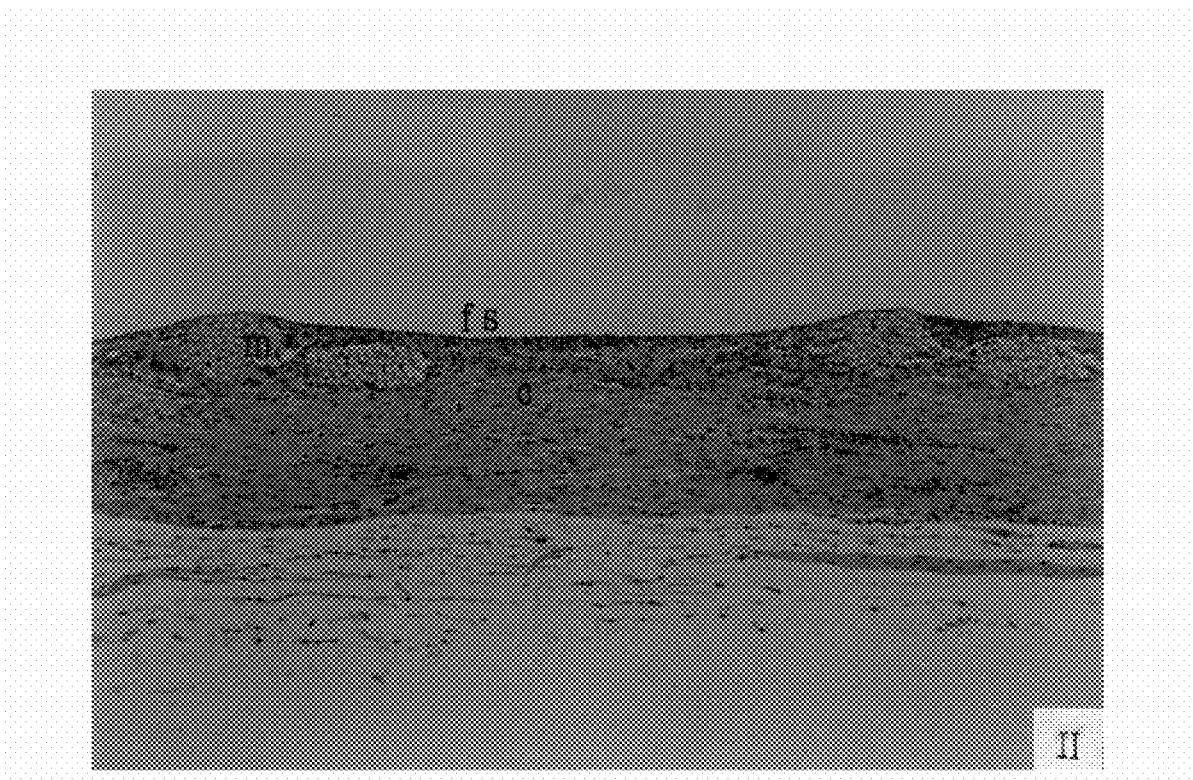
FIG. 5 is a similar diagram to FIG. 4 (H & E×40) for variation II of the current invention.

By contrast, the section through the pre-flow variation II shown in FIG. 5 shows polyester mesh bundles (M) closer together due to the increased reticulation density and collagen tissue more compact (C). There is smooth lining to the flow surface (FS) and the tissue cover over the mesh bundles remains thin, as in variation I.

Figure 6:
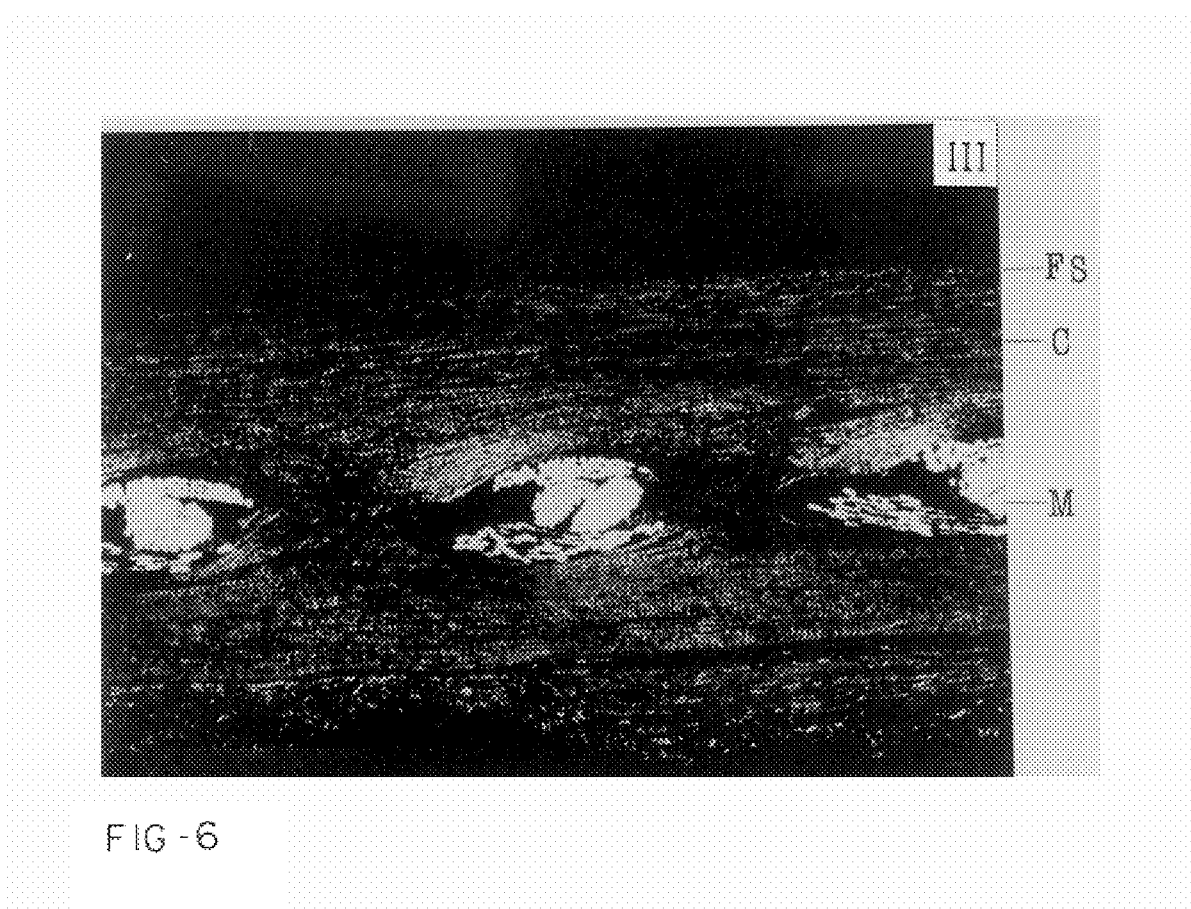
FIG. 6 is similar to FIG. 4 for variation III of the current invention.

In variation III shown in FIG. 6, the polyester mesh bundles (M) are completely incorporated within the collagenous tissue (C) which is very compact. The mesh bundles are slightly closer again, and the flow surface (FS) remains smooth. The tissue cover over the flow surface is thick. This is due to the looseness of the fitting of the mesh over the mandril which allows more tissue to invade the space between the mesh and the mandril compared to the stretched mesh configuration of variation I.

Figure 7:
FIG. 7 is similar to FIG. 4 for variation IV of the invention described hereunder.

The section through the pre-flow variation IV as shown in FIG. 7, shows that the polyester and polyurethane mesh bundles (M) are well incorporated into the dense collagen tissue (C). The mesh bundles are very closely aligned. The strength imparted by the thickness of the tissue cover and closely aligned mesh bundles indicate a non-vascular application for this variation would be appropriate.

Figure 8:
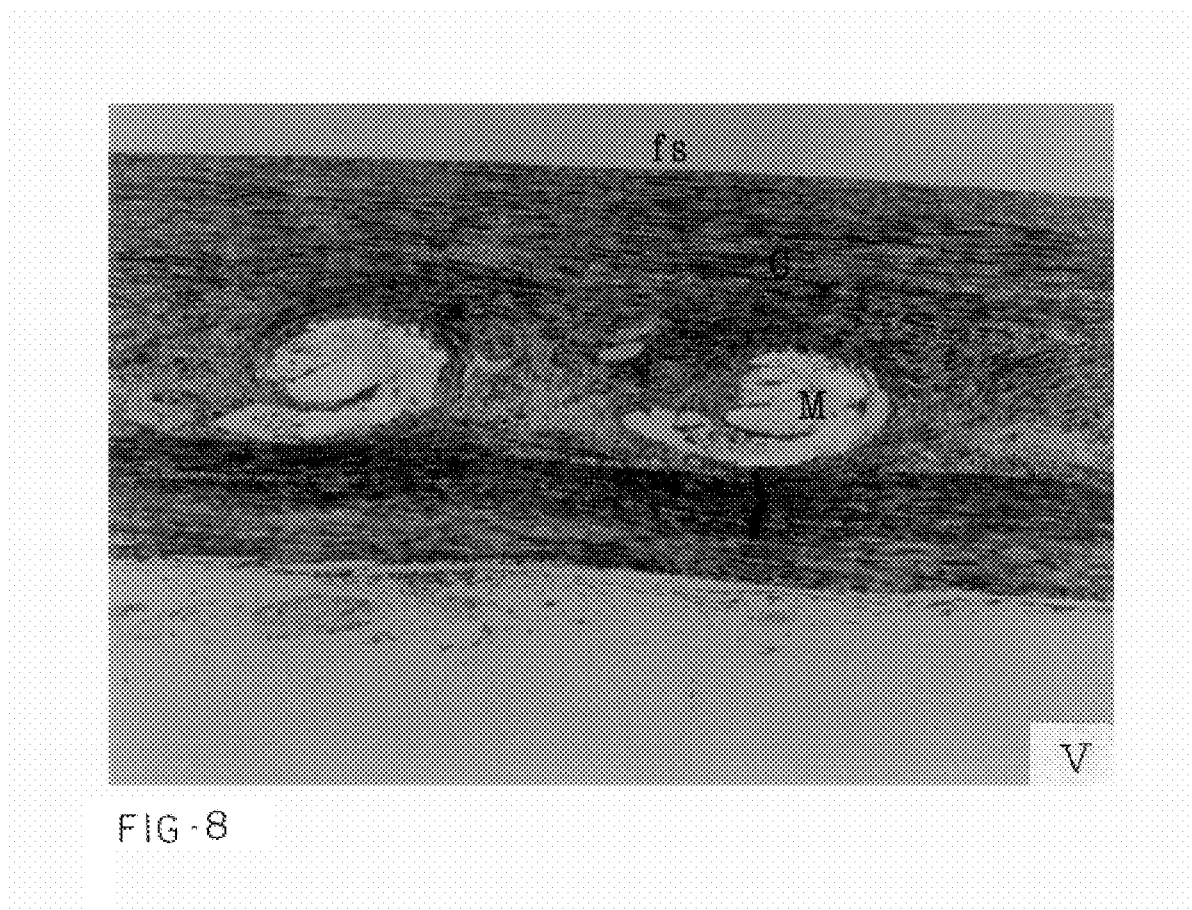
FIG. 8 is similar to FIG. 4 for variation V of the invention described hereunder.

With reference to FIG. 8 where variation V is shown, the polyester mesh bundles are dipped in polyester (M) and are closely aligned and well incorporated into the collagen tissue (C).

Figure 9:
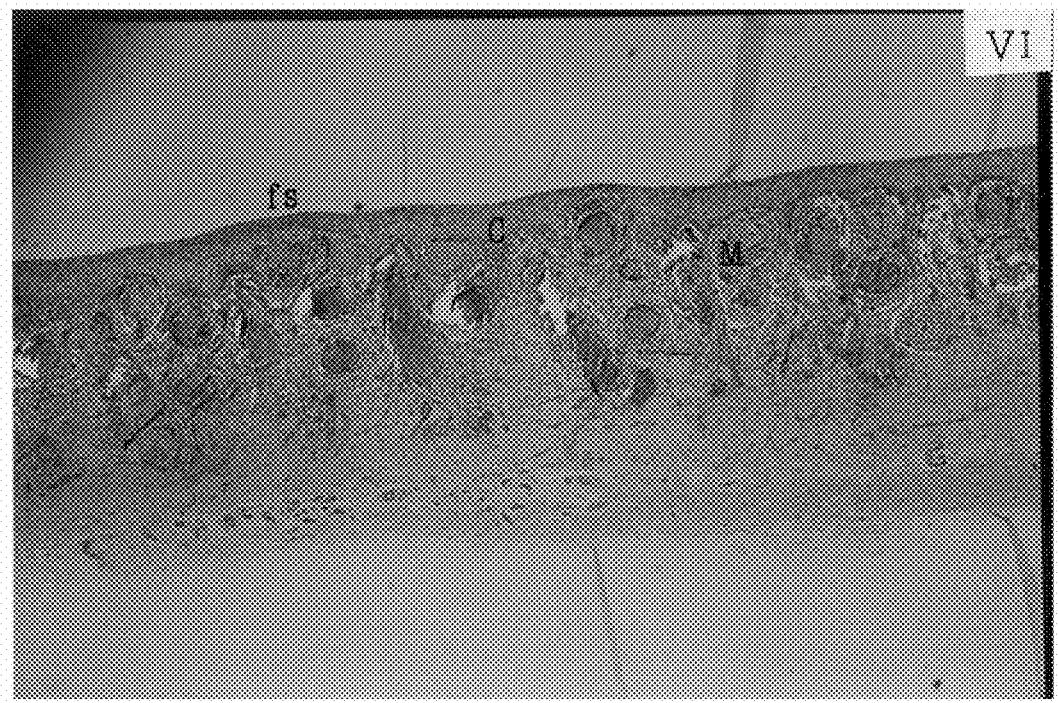
FIG. 9 is similar to FIG. 4 for variation VI of the invention described hereunder.

With reference to FIG. 9 where variation VI is demonstrated, the polyurethane strands wound around the polyester mesh (M) result in bundles which are well incorporated into the dense collagen tissue (C). The physiochemical characteristics obtained with variation I have been retained in variations II and III with some notable differences listed in Table 1 below.

TABLE 1

In vitro studies which demonstrate the improved characteristics of variation III.

| Study | Variation II | Variation III |
|---|---|---|
| Haemocompatibility | 16.44 +/− 7.3 | 10.36 +/− 7 |
| (Platelet consumption - The lower the number the more haemocompatible). | | |
| Extension | 2.77 +/= .68 | 5.71 +/− 2.32 |
| Kink radius | 15–19 | 9–15 |
| (The lower the number the greater resistance to kinking). | | |
| Instron test | 85.25 +/− 43 | 125.2 +/− 47 |

Figure 10:
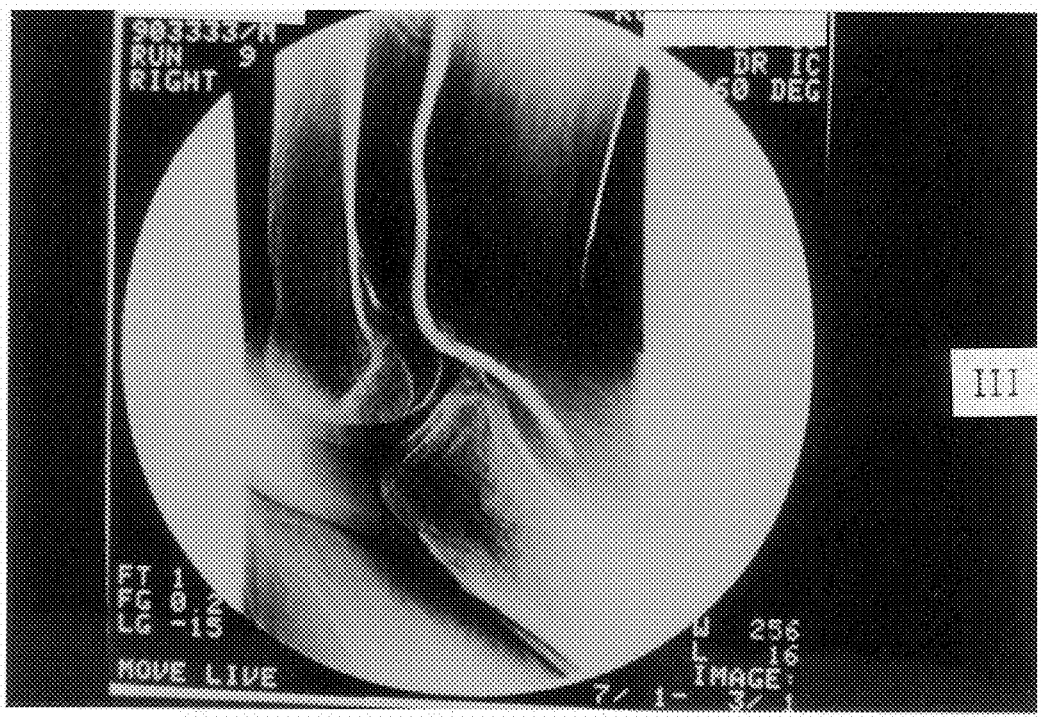
FIG. 10 is an angiogram of a variation III prosthesis in the below knee femoropopliteal position in the human passing across the bent knee.

The haemocompatibility as determined by the platelet consumption study using a closed loop system has been enhanced in variation III. The lower the reading the more haemocompatible the surface. Instron testing exposes the material to stretching forces. Variation III has greater strength, desirable in some non-vascular applications. Variation III demonstrates increased longitudinal stretch or elasticity (extension) and greater kink resistance required in a vascular prosthesis as it allows for better placement around the knee joint or other areas where curving is desirable as demonstrated in the human angiogram in FIG. 10.

Animal studies undertaken with variation I, II and III in the aorto-iliac position in dogs to determine patency and long term performance have demonstrated excellent results (Table 2 below).

TABLE 2

In vivo studies comparing Variation I, II and III in the aorto-iliac position in the canine model.

| Prosthesis type | no. of dogs | days patent | % patency |
|---|---|---|---|
| Variation 1 | 10 | 308–420 | 100% |
| | 42 | 1–730 | 80% |
| Variation II | 63 | 63–>1460 | 87% |
| | 47 | 365–>1095 | 80.8% |
| Variation III | 10 | 28–195 | 90% |
| | 12 | 28–373 | 100% |

Variation III demonstrates a thicker tissue cover on the flow surface and over the mesh bundles compared to variation II as FIGS. 11a and 11b, 12a and 12b and 13 show, indicating an improved flow surface and reducing the risk of prosthesis failure.

Figure 14A:
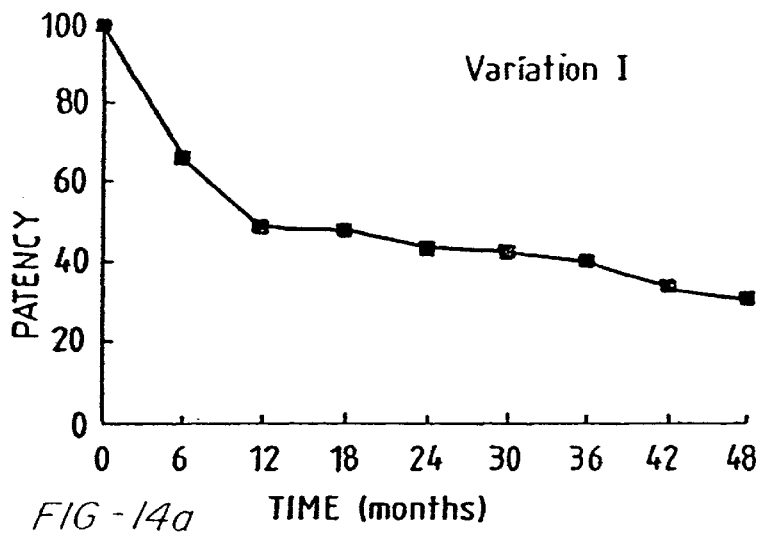
FIG. 14a shows the cumulative patency of 73 variation I prostheses in the femoropopliteal position.
Figure 14B:
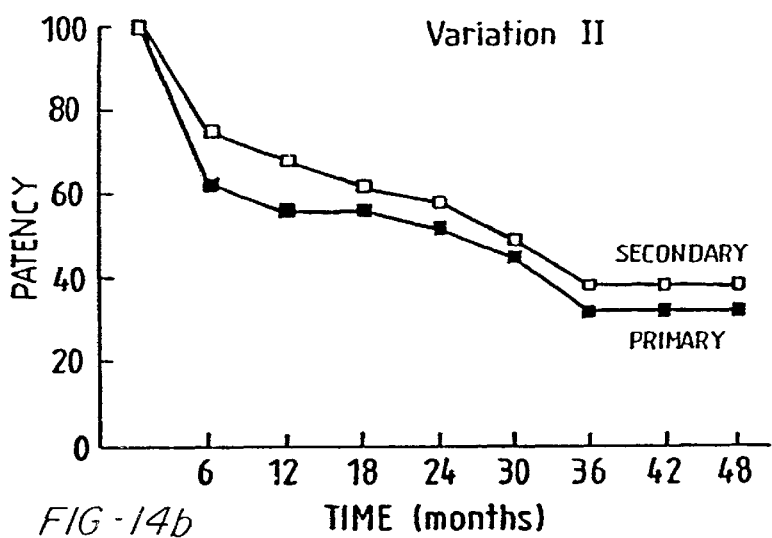
Figure 14C:
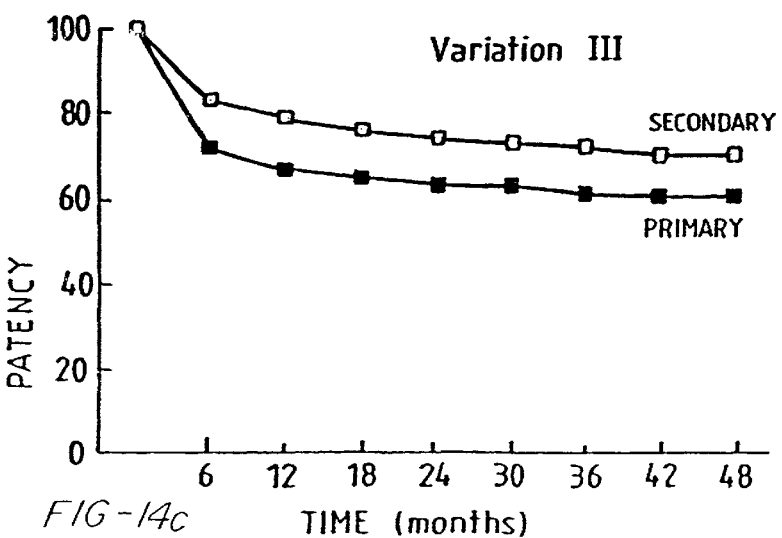
FIG. 14c shows the primary and secondary patency in the study undertaken by the same surgical unit as in FIG. 14a on 79 variation III prostheses.

Variation I, II and III have been evaluated in human clinical studies for peripheral revascularisation in one surgical centre and the results are shown in FIGS. 14a, 14b and 14c. The results obtained at four years are superior in Variation III with fewer occlusions occurring in the early time frame, thus documenting demonstrable enhancement in performance as a direct consequence of the modifications incorporated.

Figure 11A:
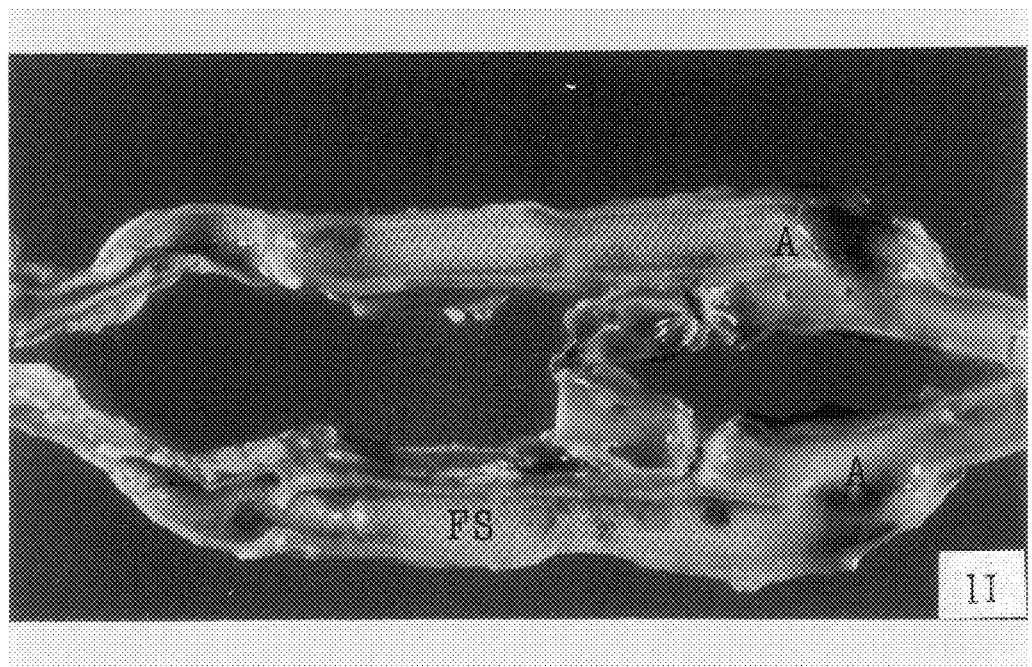
FIG. 11a is an explanted variation II prosthesis after seven months in the aorta-iliac position in a canine patient.
Figure 11B:
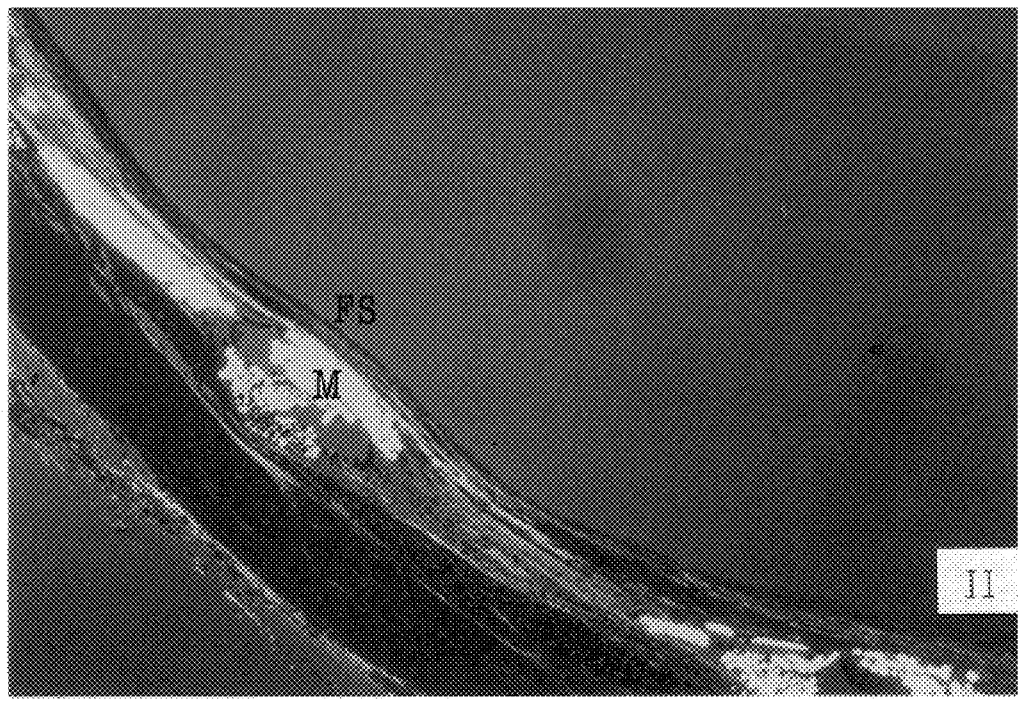
FIG. 11b is a reproduction photomicrograph of a section through the prosthesis of FIG. 11a, Sirius Red X 10.

With reference to FIG. 11, an explanted variation II prosthesis after seven months in the aorta-iliac position in the canine model is shown. Blood staining has occurred at the anastomoses (A) due to the thin tissue cover over the mesh on the flow surface (FS). The prosthesis was patent at explant. With reference also to FIG. 11b, the flow surface (FS) is smooth and thrombus free however the tissue cover over the mesh (M) is thin.

Figure 12A:
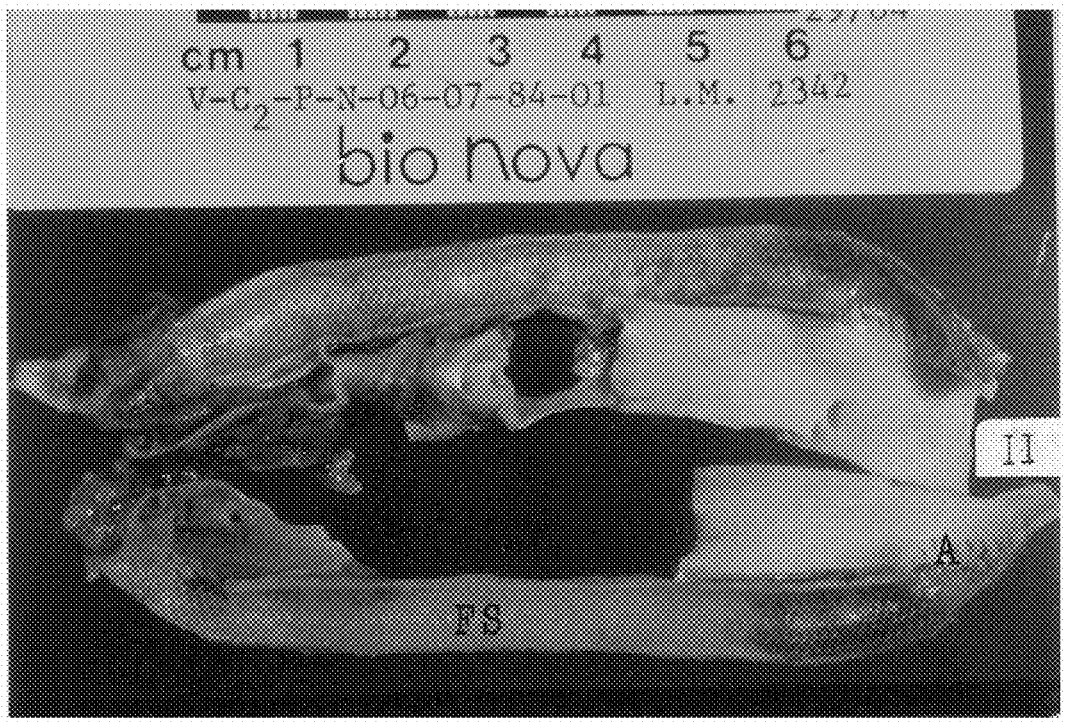
FIG. 12a is a explanted variation II prosthesis similar to FIG. 11a after four years in a canine host.
Figure 12B:
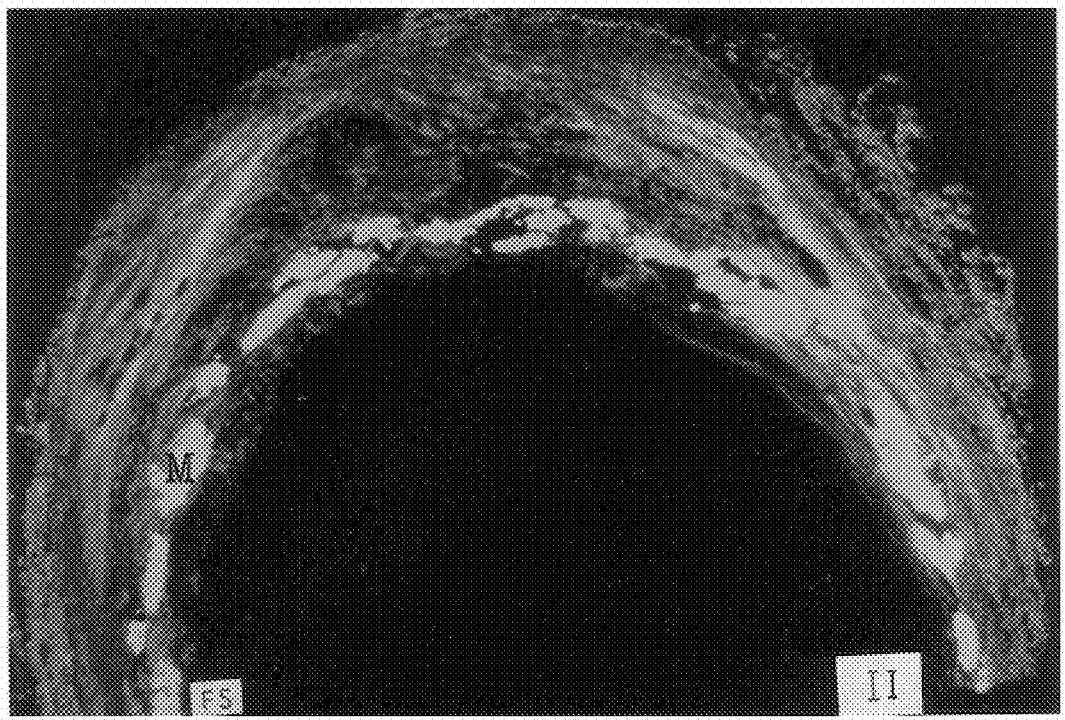
FIG. 12b is a reproduction photomicrograph of a section through the prosthesis of FIG. 12a, Sirius Red X 10.

FIG. 12a and 12b shows that the same characteristics are present at seven months and four years in the canine model for variation II.

Figure 13:
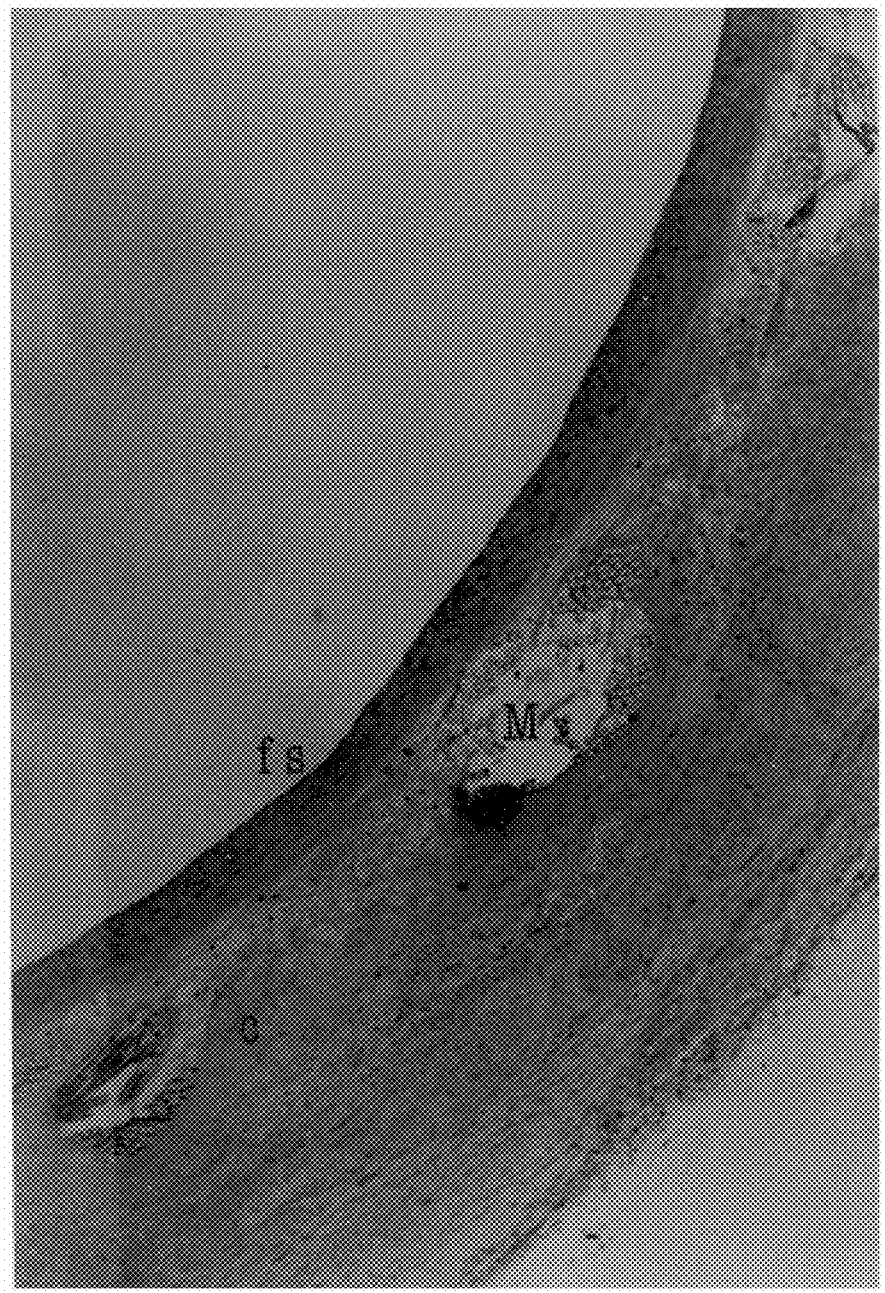
FIG. 13 is a reproduction photomicrograph of a section through a variation III prosthesis after six months in the aorta-iliac in a canine host, H & E×40.

A variation III prosthesis in the canine model is shown after six months in the aorta-iliac position in FIG. 13. The flow surface (FS) is thrombus free and the tissue cover over the mesh (M) is thick preventing the occurrence of blood staining.

Variations I, II and III have been evaluated in human clinical studies for peripheral revascularisation in one surgical centre and the results are shown in FIGS. 14a, 14b and 14c. The patency at 48 months for variation I is 32%. A large number of failures occurred in the first and second six month periods indicating a less than optimal flow surface to the prosthesis.

FIG. 14b for variation II prosthesis shows little change from variation I in the primary patency at the six and 48 month time period, though the secondary patency at the six month period is satisfactory.

The primary and secondary patency of variation III prosthesis shown in FIG. 14c indicates that the improvements in the technology for variation III have transferred to markedly improved clinical performance.

The results obtained at four years are superior in variation III with fewer occlusions occurring in the early time frame, thus documenting demonstrable enhancement in performance as a direct consequence of the modifications incorporated in variation III. The improvements in variation II are less dramatic.

Figure 15A:
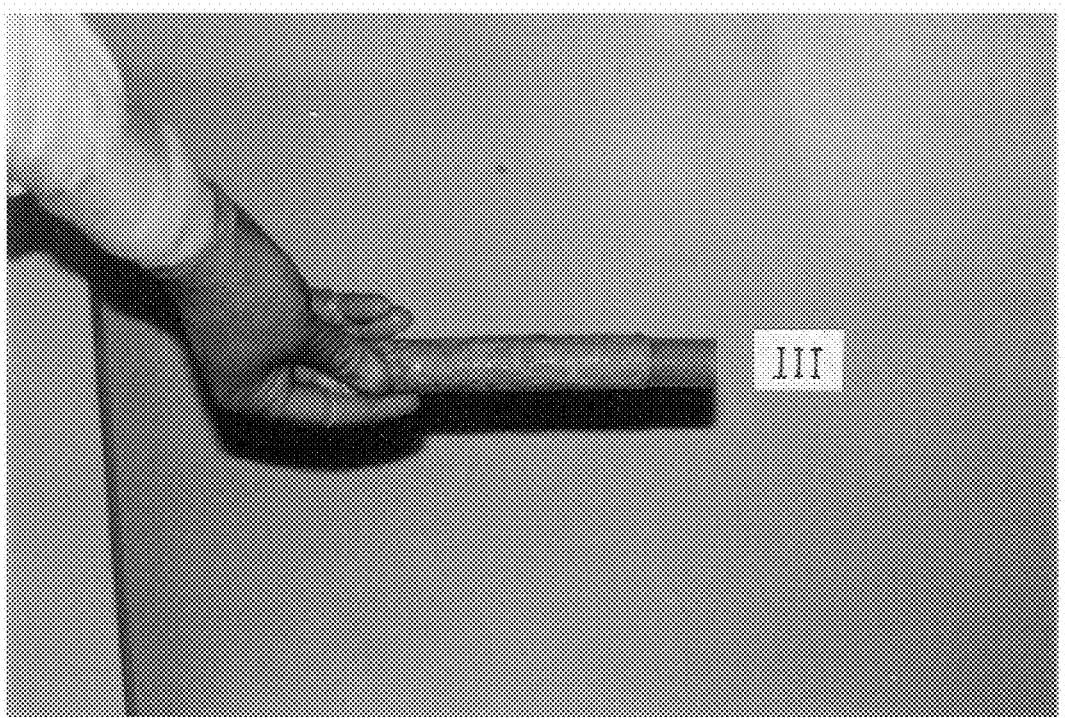
FIG. 15a shows a wide diameter variation III prosthesis suitable for production of a flat sheet after removal from the host animal.
Figure 15B:
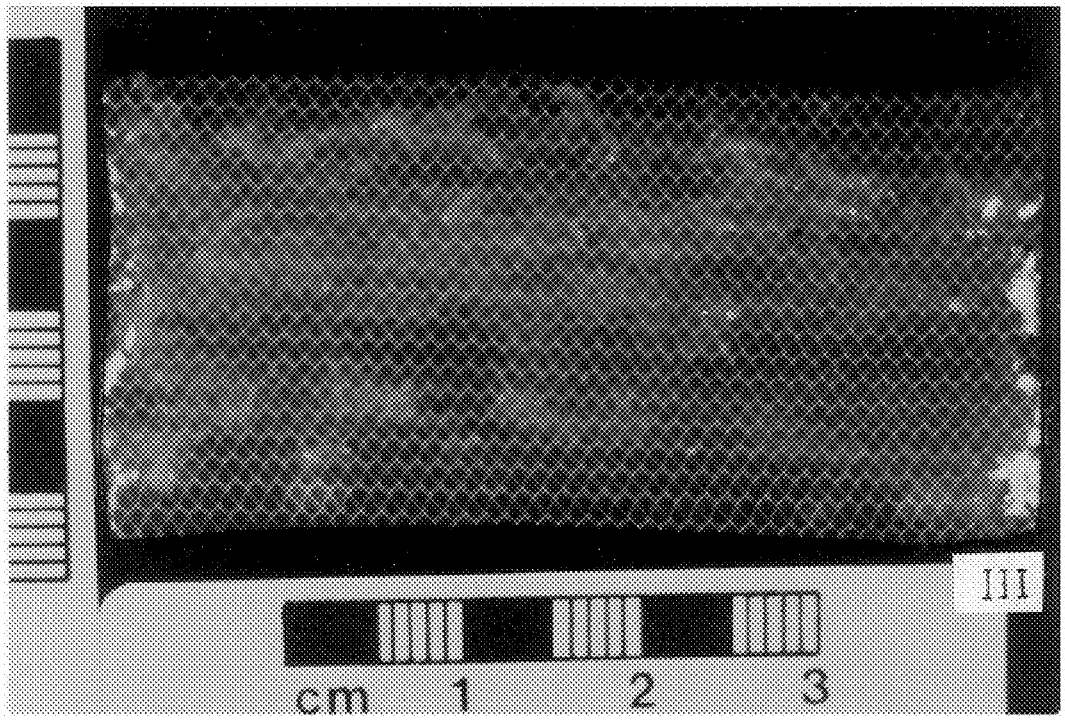
FIG. 15b shows the variation III prosthesis of FIG. 15a cut longitudinally and laid flat ready for processing.

The sheet form of the biomaterial is shown in FIGS. 15a and 15b, where a large-diameter variation III prosthesis was manufactured. The flat material was produced by cutting the tubular prosthesis along its length. Such a prosthesis can alternatively be manufactured in accordance with the third aspect of the invention by implanting in the host animal a sheet support and covering the sheet on both sides by the synthetic material, either in mesh form or alternatively in a painted particulate form.

Figure 16:
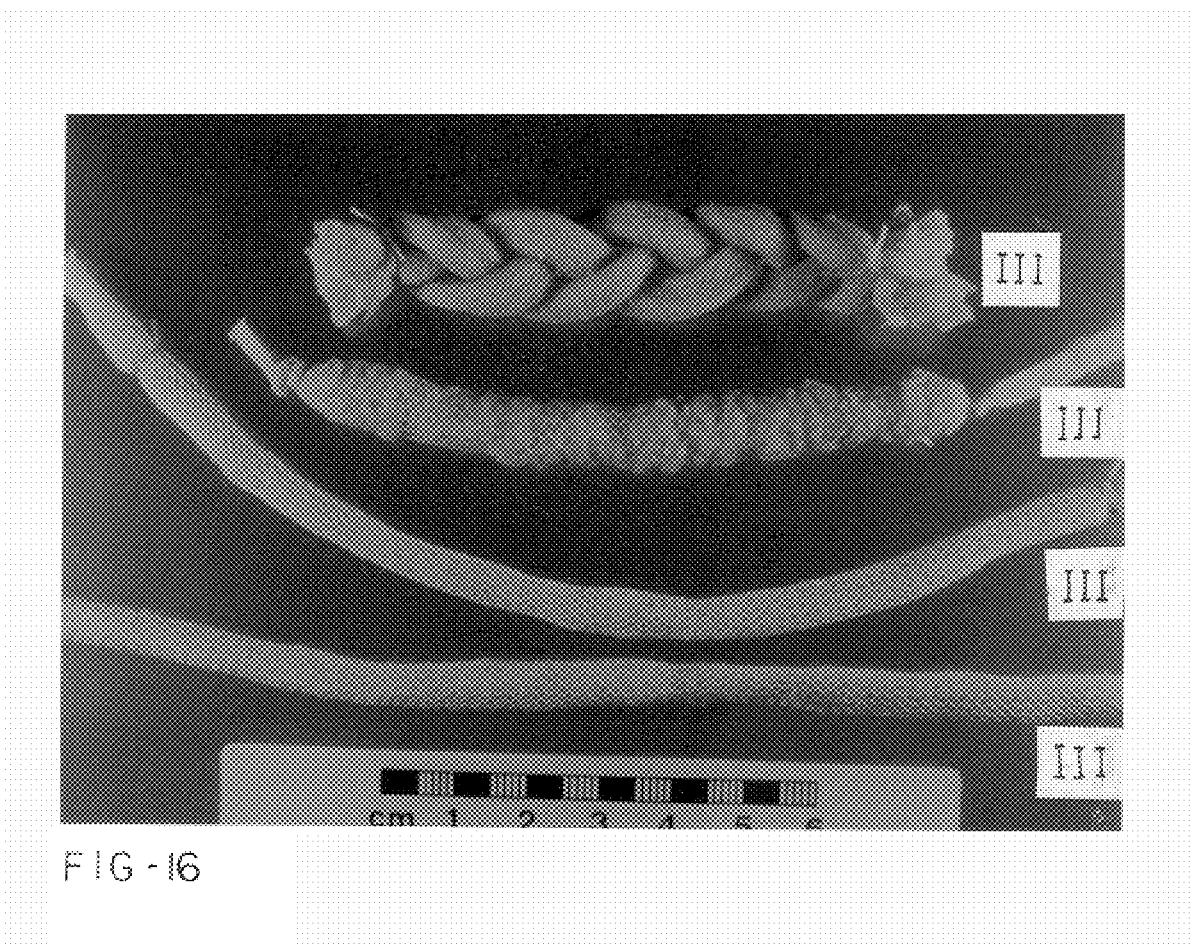
FIG. 16 shows various shapes of variation III prostheses which can be produced for different applications such as ligaments.
Figure 17:
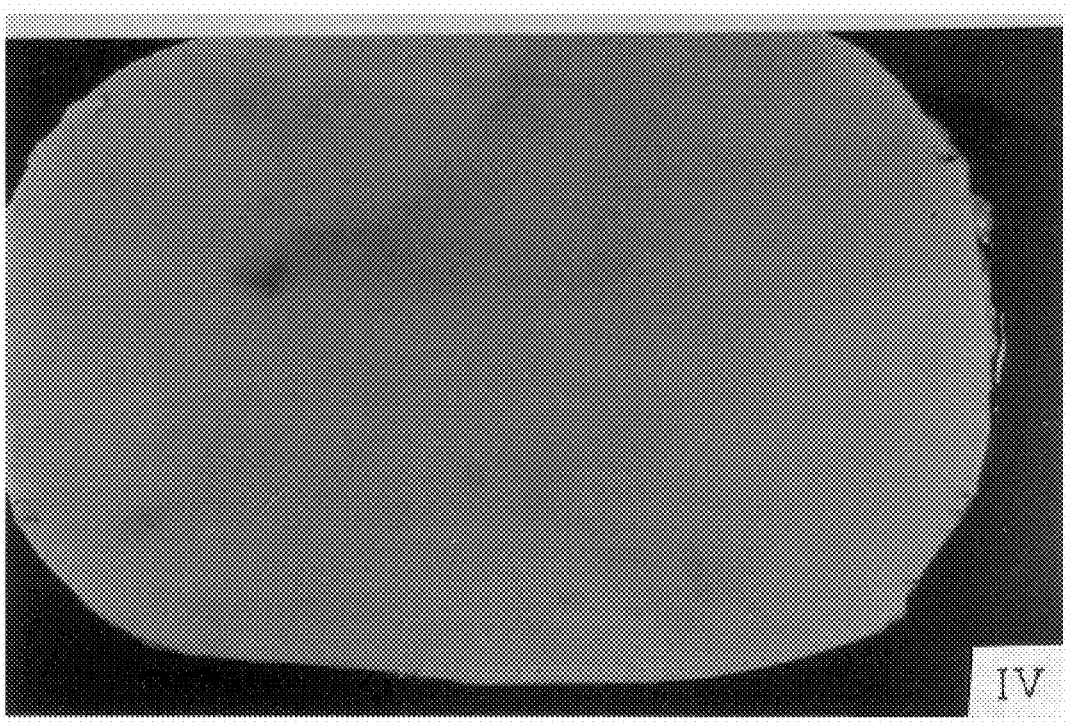
FIG. 17 shows a variation IV "bladder" prosthesis suitable for lining an artificial heart, produced in accordance with an embodiment of the invention.
Figure 18:
FIG. 18 shows a variation IV oval shaped patch on its rough side, suitable for body wall patching.

Such prostheses produced from flat sheets by either method would be useful in non-vascular applications such as ligament replacement where strength is a critical consideration. Variations in shape and configurations are shown in FIG. 16. Flat rectangular or oval shaped silicone, nylon, acrylic, polyethylene, teflon or polyurethane support sheets in isolation or in combination covered with synthetic mesh results in a bladder, pouch or pocket suitable for many applications (FIGS. 17, 18). The most important of them would be an application as a lining for artificial heart chambers. Unique features of an internal, smooth, haemocompatible surface shown in FIG. 17 and external non-smooth surface shown in FIG. 18 makes this aspect of the invention extremely useful in applications where attachment to external surfaces and non-attachment of the internal surface is required, as for example in hernia repair (FIG. 18).

Increased tissue cover obtained has transformed some disadvantages encountered in the original version into additional desirable features.

Figure 19:
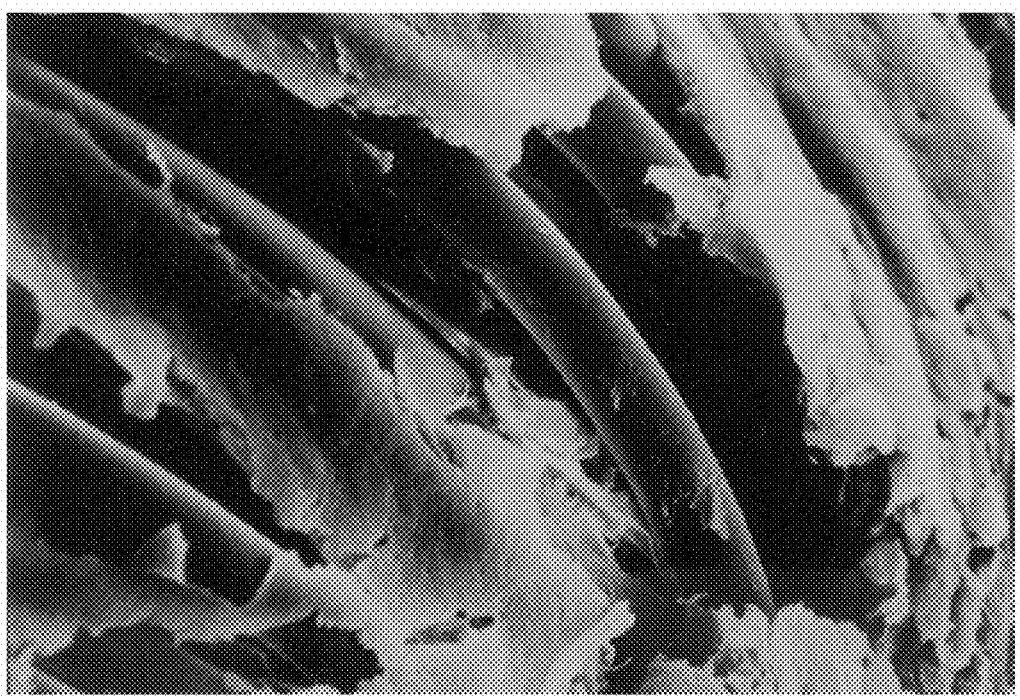
FIG. 19 is a scanning electron micrograph at 400 times magnification demonstrating cracking of tissue in variation I.

In U.S. Pat. No. 4,319,363, the prosthesis was stored in 90% absolute alcohol. This caused dehydration of the tissue component and necessitated rehydration prior to surgical implantation. In addition, in the original version, because of the thin tissue cover, with dehydration "cracking" occurred, often exposing the polyester through the tissue covering the flow surface, resulting in poor performance (e.g., in the variation I material shown in FIG. 19). The current version with increased tissue cover does not exhibit polyester at the flow surface.

In addition, during rehydration, instead of physiological saline, heparin is preferably used in the current invention and remains bioactive in the collagen/glutaraldehyde complex of the prosthesis enhancing performance. Tables 3 and 4 below show the results of heparin uptake studies. Heparin uptake and retention directly and following initial protamine sulphate treatment were studied. Heparin retention was assayed after 120 hours (5 days). Heparin uptake and retention were superior with PrSo4 treated grafts but it caused stiffness that made it less satisfactory. The direct method which consisted of partial dehydration resulted in a satisfactory prosthesis. Variation III that was tested, as claimed, can retain heparin in effective amounts opening the drug delivery potential in a controlled manner.

dehydration will enable the prosthesis to be moisture packed rather than fluid packed for end use.

The tanning procedure of the current invention is identical to that described in U.S. Pat. No. 4,319,363.

Variations may be made to the current invention as would be apparent to a person skilled in the art of biomaterial design similar to that described in U.S. Pat. No. 4,319,363. These and other modifications may be made without departing from the ambient of the invention, the nature of which is to be ascertained from the foregoing description, figures and tables and the claims.

What is claimed is:

1. A biomaterial suitable for use in surgery in a human patient, comprising:
    a coherent layer of non-human collagenous tissue which has been subjected to glutaraldehyde tanning so as to comprise cross-linked collagen fibrils, and
    a reinforcement of synthetic material embedded within the coherent layer, said synthetic material having structure features for promoting said embedding, said synthetic material having on average in situ more than 50 of said features per square centimeter.

2. A biomaterial as claimed in claim 1 having more than 100 of said features per square centimeter.

3. A biomaterial as claimed in claim 1 wherein the synthetic material is a fibre mesh and the features for promoting said embedding are the reticulations of the mesh.

TABLE 3

$^3$H-heparin (cpm/m) in the lumen of graft segments

| GRAFT | BINDING PROCEDURE | $^3$H-HEPARIN IN LUMEN (cpm/ml) × $10^6$ | | | | | | DIFFERENCE IN $^3$H-HEPARIN CONCENTRATION AFTER FIVE DAYS (cpm/ml) × $10^6$ |
|---|---|---|---|---|---|---|---|---|
| | | INITALLY | | | AFTER FIVE DAYS | | | |
| | | | | AVERAGE | | | AVERAGE | |
| Var. III | Direct | 3.04 | 3.17 | 3.10 | 1.49 | 1.52 | 1.51 | 1.59 |
| Var. III | Protamine Sulphate | 3.04 | 3.17 | 3.10 | 0.97 | 1.01 | 0.99 | 2.11 |

TABLE 4

$^3$H-heparin (cpm/cm$^2$) bound to graft segments.

| GRAFT | BINDING PROCEDURE | $^3$H-HEPARIN BOUND TO GRAFT (cpm/cm$^2$) × $10^6$ | | |
|---|---|---|---|---|
| | | | | Average |
| Var. III | Direct | 0.29 | 0.24 | 0.27 |
| Var. III | Protamine Sulphate | 0.26 | 0.25 | 0.26 |

The aldehyde and amino groups in the collagen/glutaraldehyde complex can not only retain heparin but other pharmacological agents such as antibiotics, e.g., tetracycline. The increased tissue cover combined with alcohol 4. A biomaterial as claimed in claim 3 wherein the mesh is embedded in the coherent layer such that the mesh structure is in a loose unstretched state.

5. A biomaterial as claimed in claim 3 wherein the fibre mesh is constructed from polyester yarn.

6. A biomaterial as claimed in claim 5 wherein the polyester yarn is augmented with polyurethane.

7. A biomaterial as claimed in claim 6 wherein the polyurethane is in the form of strands of the polyester dipped in polyurethane.

8. A biomaterial as claimed in claim 6 wherein the polyurethane is in the form of strands of polyurethane wound around strands of the polyester.

9. A biomaterial as claimed in claim 1 wherein the synthetic material is particulate in nature.

10. A biomaterial as claimed in claim 9 wherein said features are constituted by individual particles of that material.

11. A biomaterial as claimed in claim 1 wherein the biomaterial is formed in the shape of a tube.

* * * * *